United States Patent [19]

Capps, II

[11] Patent Number: 4,571,078
[45] Date of Patent: Feb. 18, 1986

[54] QUICK DISASSEMBLY FLOWCELL

[76] Inventor: Rodney D. Capps, II, 1274 Shevchenko Dr., Ann Arbor, Mich. 48103

[21] Appl. No.: 473,902

[22] Filed: Mar. 10, 1983

[51] Int. Cl.[4] .............................................. G01N 1/10
[52] U.S. Cl. .................................... 356/246; 356/440
[58] Field of Search ................. 356/246, 440; 250/576

[56] References Cited

U.S. PATENT DOCUMENTS 3,614,243  10/1971  Harvey ................................. 356/246
3,740,158   6/1973  Bellinger et al. ..................... 356/246
4,260,257   4/1981  Neeley et al. ........................ 356/246

Primary Examiner—Davis L. Willis
Assistant Examiner—Matthew W. Koren
Attorney, Agent, or Firm—Stephenson and Boller

[57] ABSTRACT

A new and improved flowcell comprises an interposed fluid pathway, coaxial with the light path of a fiber optic system and consisting of two or more units combined by means of intereference-fit joints which both accurately align the bores and seal against leakage. The joints are so fashioned that the flowcell may be quickly disassembled to permit cleaning or removal of lint fibers, crystals or other minute materials which typically deposit and obstruct both solution flow and light transmission. At each end of the fluid pathway, a short rod of a clear material of broad spectral transmissivity such as quartz, fused silica, sapphire, etc., acts as a fluid seal and window to the fluid pathway. Fluid enters and exits the pathway by means of ports located at right angles to the light path. The flowcell mounts on a holder.

17 Claims, 6 Drawing Figures

QUICK DISASSEMBLY FLOWCELL

BACKGROUND AND SUMMARY OF THE INVENTION

This invention relates to a flowcell which may be generally defined as a device used in spectrophotometry, transparent to an energy source, carrying a solution stream, and placed in a path between a monochromatic light source and detection system for the purpose of measuring changes in the optical absorbance or light transmissivity of the solution stream.

Flowcells are commonly used in fluid analyzers having spectrophotometers or colorimeters. A colorimeter or spectrophotometer is a device for measuring the optical density or light transmissivity of fluids, solutions, or gases; either in stasis or in dynamic flow. Light at selected wavelength, over the visible and/or ultraviolet wavelengths, passes through a flowcell. In particular, the light passes through a solution, or fluid, flow passage of the, flowcell carrying the fluid, or solution, being analyzed. The sample being analyzed modulates, or attenuates, the input light so as to yield a light output from the flowcell which is representative of a particular characteristic of the fluid, or solution, being analyzed. The light output is detected and electrically processed to provide an electrical signal which in turn provides intelligible information representative of the particular characteristic of the fluid, or solution.

In some analyzers a multitude of analyses may be made on a time-shared basis and therefore it is common to employ large numbers of flowcells each of which receives an input light and provides a corresponding light output representative of the particular characteristic being analyzed.

Previous flowcells comprise transparent bodies disposed at various locations within the analyzer to which fluid carrying conduits are connected. Each flowcell comprises a fluid inlet and a fluid outlet which may take the form of nipple-like fittings. Specifically, such nipple-like fittings comprise circular tubes axially spaced apart and projecting radially of the main cylindrical body of the flowcell. The path of fluid through a flowcell is radially inwardly through one fitting into a radial bore within the flowcell body, then axially along a central axial bore within the body to another radial bore which carries the fluid radially outwardly to exit through the other fitting. The fluid carrying conduits, or lines, to and from the flowcell are typically flexible hoses fitted over the ends of the nipple-like fittings. The inlet and outlet fittings of prior flowcells are circumferentially aligned, being lodged into circumferentially aligned radial bores in a unitary portion of the flowcell body. It has also heretofore been the practice to fixedly mount the body of the flowcell on a suitable holder which is in turn used to mount the flowcell within the analyzer.

In the prior flowcells light from a suitable source is supplied to one axial end of the flowcell body. The light is conducted to the flowcell by a suitable medium, such as an optical fiber, so as to enter one end of the central axial bore through the flowcell body. The light thereafter passes through the fluid as it flows axially through the flowcell, and having been attenuated or modulated by the particular characteristic of the fluid being analyzed, the light exits via the opposite axial end of the flowcell body. The exiting light is conducted away via an optical fiber at the opposite axial end of the flowcell body to additional components of the colorimeter for processing to ultimately develop the intelligible information representative of the particular characteristic of the fluid which is being analyzed by this particular flowcell.

An analyzer contains various other components in addition to flowcells. As such, these are usually contained within a console, or housing, and the flowcells are distributed throughout the housing in various locations, or in banks. With the prior flowcells, certain of these locations are often inaccessible for making connections with the flowcells. Hence, if a flowcell needs to be removed and replaced, it is often a difficult task to perform the removal and replacement because of the presence of additional components in the vicinity and close quarters.

Moreover, the construction of the prior flowcells necessitated replacement of a clogged flowcell by a new one. In other words, cleaning of a clogged flowcell was impractical, and the clogged flowcell was scrapped. Prior flowcells are beset by further problems; one such flowcell is an extremely delicate unit subject to easy breakage due both to: (a) inherently fragile material (glass) and (b) joining of materials traditionally incompatible (glass and metal). In use, any damage to the flowcell is typically catastrophic. If dropped, it is destroyed instantly: if there is a slight misalignment of the fiber optic calipers, the metal light masks are stressed and will soon break away from the body or the body will separate from the metal mount. If great care is not exercised in making connections to its glass entry/exit ports, they are easily snapped off. Optical quality is not uniform, varying by up to 30% in transmitted light from unit to unit.

The present invention is directed to a new and improved flowcell which possesses important advantages and benefits over prior flowcells of the type described above.

One important advantage of the present invention is that the flowcell can be quickly disassembled into two halves for convenient cleaning and unclogging when needed. Hence, it is unnecessary for a clogged flowcell to be discarded and replaced by a new one. This can yield a savings to the user of flowcells.

Another important advantage of the invention is that the construction of the flowcell provides for more convenient installation, and replacement, particularly in regard to connection of lines to the flowcell. In this regard the flowcell is endowed with a capability whereby the inlet and outlet ports may be relatively positioned with respect to the axis of the flowcell body independently of each other and the flowcell body itself may be independently adjusted relative to its holder. Thus, in an installation where it may be difficult or indeed impossible to make connections to a prior type of flowcell, a flowcell embodying principles of the present invention can be easily adjusted so that its connections and mounting can be more expeditiously and easily accomplished.

Briefly, the flowcell of this invention comprises an interposed fluid pathway, coaxial with the light path of a fiber optic system and consisting of two or more units combined by means of interference-fit joints which both accurately align the bores and seal against leakage. The joints are so fashioned that the flowcell may be quickly disassembled to permit cleaning or removal of lint fibers, crystals or other minute materials which typically deposit and obstruct both solution flow and light transmission. At each end of the fluid pathway, a short rod of a clear material of broad spectral transmissivity such as quartz, fused silica, sapphire, etc., acts as a fluid seal and window to the fluid pathway. Fluid enters and exits the pathway by means of ports located at right angles to the light path.

The foregoing features, advantages, and benefits of the invention, along with additional ones, will be seen in the ensuing description and claims which should be considered in conjunction with the accompanying drawings. The drawings disclose a preferred embodiment of the invention according to the best mode contemplated at the present time in carrying out the invention.

DESCRIPTION OF THE PREFERRED EMBODIMENT

Figure 1:
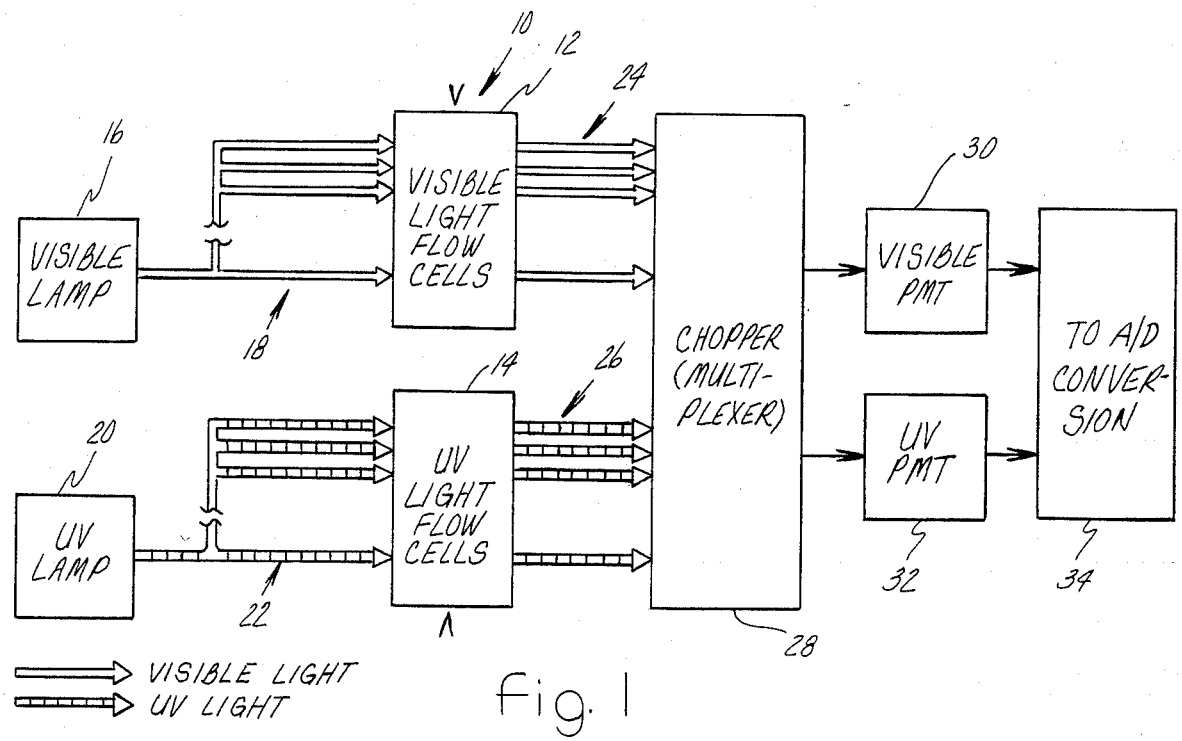
FIG. 1 is a block diagrammatic view of a portion of an analyzer illustrating exemplary usage of flowcells.

FIG. 1 illustrates in block diagram form a portion of an analyzer in which flowcells are used. In the disclosed embodiment the analyzer comprises an analytical cartridge section 10 which contains a plurality of flowcells. By way of example these are identified in FIG. 1 as a series of visible light flowcells 12 and a series of ultra-violet light flow cells 14. The flowcells themselves will be shown in detail in the subsequent drawing figures.

Fluids, or solutions, being analyzed are conducted through the individual flowcells by additional apparatus of the analyzer which is not illustrated in FIG. 1. That apparatus comprises various components which are utilized to pump the fluid, or solution, samples through the flowcells in a suitable and predetermined fashion. Light is conducted through appropriate fibers of a fiber optic bundle to the respective individual flowcells. Visible or white light is provided from a visible lamp source 16 and conducted via fibers of the fiber optic bundle 18 to the individual visible light flowcells 12. In similar fashion, an ultra-violet lamp 20 supplies ultra-violet light through the individual fibers of the fiber optic bundle 20 to the ultra-violet light flowcells 14.

The samples flowing through the individual flowcells absorb a certain amount of the light passing through each flowcell. The absorption is a function of the particular characteristic being analyzed. Hence, the light output exiting each flowcell is representative of the corresponding characteristic of interest in the fluid sample. The light output is conducted by a corresponding optical fiber of an output bundle of optical fibers to subsequent components which are used to develop the intelligible information relative to the characteristics of interest. In the case of the visible light flowcells, the output light signal from each flowcell is conducted through the corresponding optical fiber of the output bundle of fibers 24, and in the case of the ultra-violet light flowcells, the corresponding output signal from each is supplied through a corresponding one of an output bundle of fibers 26.

The fibers of the two output bundles 24 and 26 are supplied as inputs to a chopper, or multiplexer, 28. This is a conventional portion of a colorimeter and may comprise a rotating wheel which is effective, in conjunction with the other controls and components of the analyzer, to process the light signals and develop corresponding output signals related to the samples analyzed in the individual flowcells. Thus, each of the visible light flowcell light signals is sequentially supplied on a repeating basis to a conversion device which is designated as a visible photomultiplier tube (PMT) 30. The PMT 30 develops corresponding analog output signals related to the characteristic of the individual flowcell samples. Similarly for the ultra-violet light signals, there is an ultra-violet PMT 32 which develops analog output signals related to each of the ultra-violet light flowcell signals.

Both PMT's are coupled to additional components to develop the intelligible information and in the illustrated embodiment a portion of this is shown as an analog-to-digital (A/D) converter 34 which converts the analog signals from the PMT's into digital information. This may be finally displayed, for example, by printing on a sheet of paper.

Thus, having described the general context of the spectrophotometer in block diagram form, it is appropriate to mention that the actual construction of the analyzer comprises the flowcells being located physically at various locations within a console or housing, either individually or in cartridge banks, and to each flowcell there must be connected two optical fibers as well as two fluid lines for conveyance of the fluid being analyzed.

Figure 2:
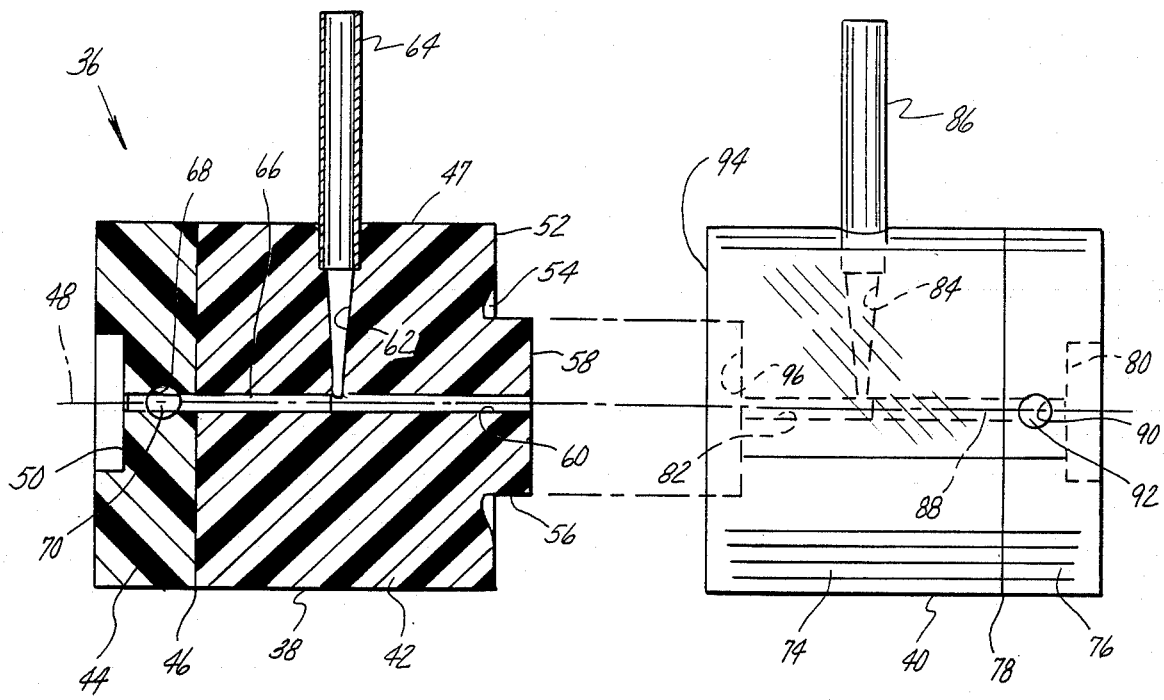
FIG. 2 is a longitudinal view of a flowcell embodying principles of the invention illustrating the disassembled condition and one portion of the flowcell in longitudinal cross section.
Figure 3:
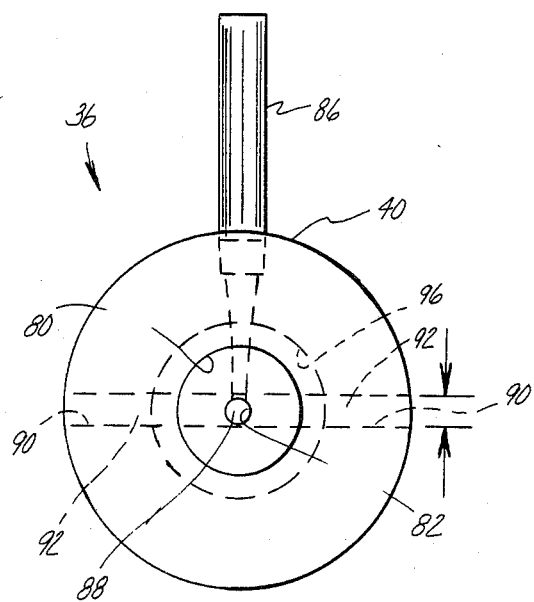
FIG. 3 is a right hand axial end view of the flowcell of FIG. 2.

FIGS. 2 and 3 illustrate details of the construction of the preferred embodiment of flowcell of the present invention designated by the general reference numeral 36. It comprises two separable halves 38 and 40.

Considering first the details of the left hand body half 38, one will observe that it comprises sections 42 and 44 which are the light mask and flowcell body welded together at matching end surfaces indicated by the numeral 46. The flowcell body has a circular outside diameter 47 and a central longitudinal axis 48. The body section 42 is a clear acrylic plastic while the body section 44 is a colored acrylic which is used to identify the particular flowcell, for example identifying the length of the light path through the fluid.

The left hand end of the body half 38, as viewed in FIG. 2, is flat and perpendicular to axis 48 except for a central circular counterbore 50 which is coaxial with axis 48. The right hand end of body half 38 comprises a flat annular region 52 forming the outer margin of the right hand end. Immediately adjoining the radially inner edge of the annular region 52 is an annular recess 54 which surrounds a circular projection 56 which projects axially to the right of the body half 38 beyond the marginal region 52. This projection terminates in a flat end face 58, both 58 and 52 being at right angles to axis 48.

A longitudinal axial bore 60 of circular cross section extends completely through the body half 38 from left to right coaxial with axis 48. The left hand end of bore 60 opens to counterbore 50 and the right hand end opens at the end face 58 of projection 56.

The section 42 of body half 38 is also provided with a radial bore 62 which tees into bore 60 in a central region of the length of the body half. The bore 62 is suitably shaped at its radially outer end segment for press-fit reception of a circular tubular walled element 64. As can be seen in FIG. 2 the lower end of element 64 is lodged within th upper or radially outer end of bore 62. Thus the tubular element 64 projects radially outwardly of the body half forming a nipple onto which the end of a flexible tube (not shown) can be inserted.

Disposed within a portion of axial bore 60 is an optical element 66 which is preferably a clear rod of circular transverse cross section. The rod 66 is of a diameter providing a very close fit within bore 60 to form a fluid seal and optical window. The length of rod 66 is chosen so that when assembled into the flowcell body, and as viewed in FIG. 2, the right hand end of the rod is located just before the T intersection of bores 62 and 60, and so that the left hand end is spaced just slightly to the right of counterbore 50. The axial ends of the rod are provided with an optical finish and the positioning of the rod in this way provides protection for its optically finished ends. The rod may be of any suitable material such as quartz, fused silica, sapphire, etc.

It is desirable for rod 66 to be secured in position by a further means which can be an epoxy. For this purpose a diametrical transverse bore 68 is provided in the body half to intercept the axial bore 60 in a region where rod 66 will be located. This bore 68 is of course created before rod 66 is inserted into bore 60. Epoxy 70 is introduced into bore 68 from both ends after rod 66 has been inserted into the body. The epoxy fills bore 68 and cures to secure the rod in place. The epoxy is spaced from the ends of the rod so that there is no opportunity for the epoxy to intrude around either end of the rod and potentially obstruct light transmission through the rod.

Looking now to the right hand half 40 of the flowcell as viewed in FIG. 2 one will observe that its construction bears many similarities that are symmetric to the left hand half 38. More specifically, the body half 40 comprises a clear acrylic plastic portion 74 and a colored portion 76 which are welded together at matching surfaces indicated by the reference numeral 78. The right hand end of the body half 40 is provided with a circular counterbore 80 similar to counterbore 50. A central axial passage 82 coaxial with axis 48 extends from counterbore 80 through the body and is open at its left hand end to meet the right hand end of bore 60 when the two body halves are assembled together in a manner which will be hereinafter described in more detail. A transverse bore 84 intercepts bore 82 in a T and a tubular element 86 is press-fitted into the radially outer end of bore 84 thereto to form a nipple fitting corresponding to the nipple fitting 64.

A clear optical rod 88 is inserted into bore 82 and positioned such that the left hand end stops just short of the intersection of bores 82 and 84 and its right hand end is inset slightly from counterbore 80. A diametrical transverse bore 90 is also provided and filled with epoxy 92 to secure rod 88 in place.

The left hand end of body portion 40 is essentially complementary to the right hand end of body portion 38. The left hand end of body portion 40 comprises a flat circular annular surface 94 which extends from the O.D. of the body to a central circular counterbore 96. The left end of bore 82 is open at counterbore 96.

The diameter of counterbore 96 and that of projection 58 are dimensioned for a press-fit engagement which allows the projection to be press-fitted fully into counterbore 96 and with the region 52 confronting the region 94, but slightly spaced therefrom. Thus, when the two halves are assembled together in this manner, the flowcell presents the outward appearance of a unitary construction with a very thin circular gap at the middle. The right hand end of bore 60 and the left hand end of bore 82 connect in fluid-tight relationship. By way of example the diameter of projection 58 may be very slightly oversized relative to the diameter of counterbore 96 and a certain resilient deformability of the material allows an excellent press-fit to be obtained. Moreover, this press-fit can be done manually by pressing the two halves together from opposite axial ends. Similarly whenever disassembly is required, it can be readily accomplished by manipulating the two halves to separate them, and for this purpose a slight bending motion may be used.

Figure 5:
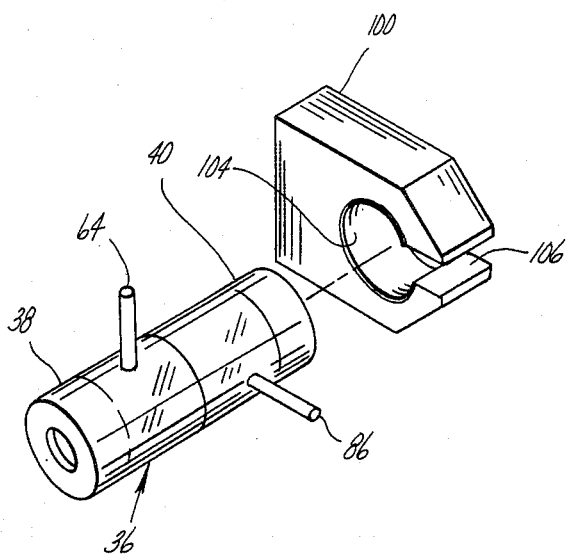
FIG. 5 is a perspective view illustrating the procedure for mounting of the flowcell in the holder.
Figure 6:
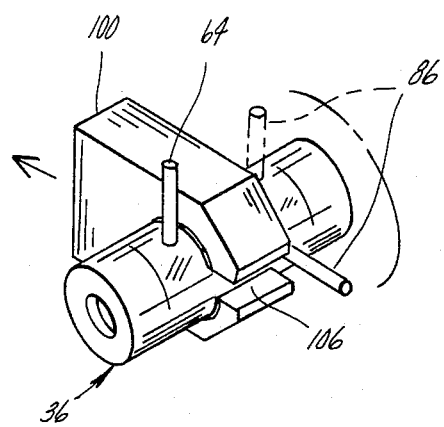
FIG. 6 is a perspective view similar to FIG. 5 illustrating the flowcell mounted in the holder.

By looking to FIGS. 5 and 6 one can see the appearance of the flowcell when the two halves are assembled together.

In use, the fluid or solution being analyzed is introduced into the flowcell from a tube connected to one of the nipples 64,86. The fluid passes through that nipple and the corresponding radial bore to pass axially of the flowcell through bores 60 and 82 between the inner ends of the two rods 66, 88. It is then conducted radially to exit via the other of the nipple fittings to which an outlet hose is connected.

Optical fibers are coupled to the right and left hand ends of the assembled flowcell as viewed in FIG. 2. In other words, one optical fiber is conducted to the left hand end of rod 66 and another optical fiber to the right hand end of rod 88. One of these optical fibers conducts light to one of the rods. The light passes through that rod exiting at the opposite end. It continues axially to the opposite rod which conducts the light to the other optical fiber. It is the light which exits the flowcell via this other optical fiber which contains the information relative to the fluid being analyzed.

Hence, during its passage through the flowcell between the ends of the two rods 66, 88, the sample under analysis attenuates the reference light. In other words, a particular characteristic of the fluid sample interacts, or absorbs light in such a way that a parameter of the light exiting the flowcell is representative of the constituent of interest in the fluid sample.

The body portions 44 and 76 are shaped to receive the optical fibers, and because said portions 44 and 76 are opaque (non-clear) acrylic, they shield the light at its points of entry to and exit from the flowcell, and prevent entry of ambient or stray light into the flow channel or optical path.

Figure 4:
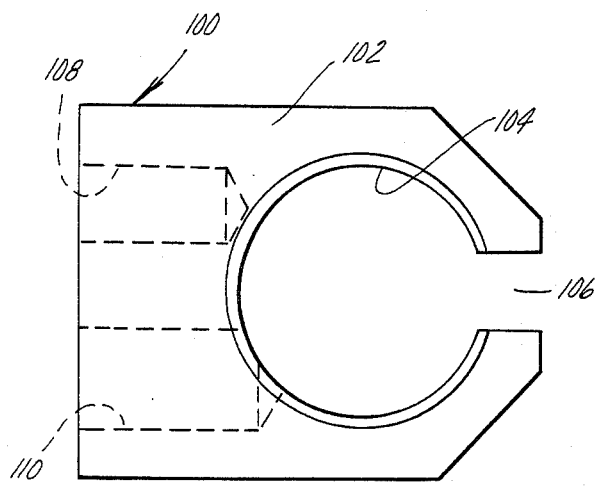
FIG. 4 is an axial end view of a holder which is used to mount the flowcell.

FIG. 4 illustrates a holder 100 which serves to mount the flowcell on the analyzer. This holder is particularly convenient because it receives and holds the flowcell without the need for any separate attaching fasteners or the like, and can itself mount in place on the analyzer without the use of fasteners. It is also convenient because it allows adjustment of the flowcell orientation.

Holder 100 comprises a molded plastic body 102 containing a circular bore 104 which embraces the O.D. of the flowcell body. (See FIGS. 5 and 6). The bore 104 does not have a continuous circumference because body 102 is provided with a throat 106 which intersects a segment of the circumference of the bore. The left hand end of the body as viewed in FIG. 4 comprises a pair of spaced apart holes 108, 110 of slightly different diameters and lengths, and these serve to mount the holder on the analyzer by press-on engagement of the bores 108 and 110 with corresponding mounting projections (not shown) in place on the analyzer. Hence, the holder can be mounted on the analyzer without separate fasteners.

FIG. 5 illustrates how the flowcell is mounted on holder 100. The flowcell body is axially aligned with bore 104 and is slid into the bore. The throat 106 provides a clearance for a nipple fitting when the two are in circumferential registry so that in the usual final assembled position as shown in FIG. 6 one of the nipples is on one side of the holder and the other is on the other side. It will be perceived that the flowcell can be slid into the holder from either direction. Of course it will also be perceived that the holder and flowcell may be first assembled together and then the holder mounted on the analyzer, or the holder can be mounted on the analyzer before the flowcell is slid into place. It will also be observed that the arrangement provides for the flowcell to be rotated within bore 104. This is a particularly convenient means to position the flowcell for ease in attachment of optical fibers and conduits, as well as to provide for clearance to other components within the analyzer which may be located within the vicinity of the flowcell.

A very important attribute of the invention which arises by virtue of its separable body halves is that the circumferential position of the two nipples may be independently set as desired. In other words each nipple may be circumferentially located at any point over a full 360° about axis 48. In the showing of FIGS. 5 and 6 the two nipples are illustrated at 90° apart. Thus each of the two nipples is independently positionable, and the flowcell itself is positionable within the holder. A still further advantage of the separable body halves is that it permits the fluid passage through the flowcell to be broken so that it can be cleaned and unclogged if the need arises. In other words, by separating the two halves of the flowcell, access is provided to bore 60 and bore 88. The radial bores and nipples are of course accessible through the ends of the nipples. With prior flowcells it was necessary to discard a clogged flowcell since there was no feasible way to clean or unclog the axial portion of the flow passage.

A still further feature of the invention is that by color coding the body portions 44, 76 so that the two halves of a flowcell of a particular size have the same color, disassembled portions can be readily identified for proper mating assembly. Such coding is especially useful where different body halves have the same dimensions at their press-fit connection (i.e. projection 56 and receptacle 96) but differ in length of the axial section of the fluid passage between the inner ends of the rods 66, 88. Several sizes of flowcell may be manufactured, each being essentially identical except for length of the axial section of the fluid passage. By coding the mating halves of each size with unique correlative indicia, i.e. making portions 44, 76 the same color for each size and each size being assigned a unique color, assembly of wrong halves should be readily apparent. One can appreciate that an incorrect length of axial flow passage will create an error in the measurement because the amount of light attenuation is a function not only of the fluid sample but also of the distance through which the light passes in the fluid. Also, the holders may be color coded to correspond to a particular flowcell as well as to aid in correct replacement of a flowcell if the holder is left in place while its flowcell is removed.

The flowcell of the invention may be fabricated using conventional fabrication procedures. For example, the acrylic plastic bodies may be fabricated by means of conventional acrylic fabrication procedures. The various bores are created also through the use of conventional procedures.

The nipple fittings are preferably stainless steel tubes pressed well into the body of the flowcell for ease in making tubing connections, and the available movement within the holder relieves any stress during connection.

The preferred construction comprises the radial bores having transverse cross sections which although circular are not of uniform constant diameter throughout their respective radial lengths. Thus in the illustrated embodiment each radial bore 62, 84 comprises a circular cylindrical counterbore into which the corresponding tubular nipple is pressed. The outer edge of the counterbore has a stress relief chamfer. From the inner end of the counterbore the bore has a narrowing diameter in the radially inward direction and may be considered as a further counterbore having an included angle for example of 14°. The end of the included angle counterbore joins to a short segment of constant circular diameter which intersects the main axial bore. The main axial bore is of a slightly larger diameter than that of the portion of the radial passage which intersects it.

While it is possible that the stainless steel and plastic of the flowcell may be slowly attacked by certain chemicals conducted in the flow of fluid through the flowcell, it is anticipated that the effective life of the flowcell of the present invention will be much longer than those of the prior art due to its more rugged construction. Moreover, the optical quality possessed by the flowcell of the invention will be equivalent to or better than those available in prior flowcells and a more consistent optical quality will be obtained in production due in large part to the better inherent alignment of the optical fibers with the bore of the flowcell.

When a flowcell is put to use the initial orientation of the inlet and outlet ports is selected by the user during assembly of the two body halves. After mounting, additional adjustment of the flowcell is possible by further rotation within the holder.

When a flowcell is removed and disassembled for cleaning, it is cautioned against use of devices and products such as sonic cleaners, wires, bleaches, strong acids, strong bases or organic solvents. In order to clean a disassembled flowcell a syringe with a short length of tubing should be connected to one of the nipple fittings and the fluid passage should be flushed and aspirated with distilled water. The two halves may then be reassembled. Before remounting of the flowcell it is suggested that the optical fibers at each end be gently dried with a cotton swab.

While a preferred embodiment of the invention has been disclosed, it will be appreciated that principles are applicable to other embodiments.

What is claimed is:

1. In a flow cell comprising a main body provided with a fluid inlet port, a fluid outlet port, and a fluid passage extending through said main body between said fluid inlet and fluid outlet ports, said main body also being provided with a light entrance, a light exit and an optical path extending through said main body between said light entrance and said light exit including a portion of said fluid passage, the improvement which comprises separably joined body portions forming said main body, one section of said fluid passage being in one of said body portions and another section of said fluid passage being in another of said body portions, said light entrance being disposed in said one body portion and said light exit in said another body portion, said optical path extending through a part of said one section of said fluid passage and also through a part of said another section of said fluid passage, said body portions being separably joined by a press-fit connection at respective confronting wall portions thereof.

2. The improvement set forth in claim 1 wherein said press-fit connection comprises a receptacle in one of said confronting wall portions and a projection in another of said confronting wall portions, said projection being press-fitted into said receptacle.

3. The improvement set forth in claim 2 wherein said confronting wall portions, said projection, and said receptacle are constructed and arrange to allow said one and said another body portions to be joined together in any circumferential relative position of one to the other over a full 360° about the axis of the flowcell.

4. The improvement set forth in claim 3 in which said fluid passage comprises a section in said one body portion extending radially of said axis and a section in said another body portion also extending radially of said axis, and inlet and outlet elements fitted each respectively into a corresponding one of said radial sections and projecting radially of the corresponding body portion relative to said axis.

5. The improvement set forth in claim 4 in which said radial sections and elements are disposed to extend radially at right angles to said axis.

6. The improvement set forth in claim 1 in which said main body comprises a longitudinal axial bore open at opposite axial ends of said main body, one portion of said longitudinal axial bore being in said one body portion and another portion of said longitudinal axial bore being in said another body portion, said optical entrance comprising an optical element disposed in said longitudinal axial bore at one axial end thereof, and said optical exit comprising an optical element disposed in said longitudinal axial bore at the opposite axial end thereof whereby one optical element is disposed in said one body portion and the other optical element in said another body portion, said portion of said fluid passage being that portion of said longitudinal axial bore which lies axially between said two optical elements.

7. The improvement set forth in claim 6 in which said fluid passage comprises radial sections each extending radially from said longitudinal axial bore respectively to a respective one of said fluid inlet and outlet ports and intercepting said longitudinal axial bore at axial locations lying between said optical elements.

8. The improvement set forth in claim 8 including in each body portion a transverse bore intercepting said longitudinal axial bore at a location which is along the length of the optical element disposed therein and including means disposed in each said transverse bore for securing the corresponding optical element in place within said longitudinal axial bore.

9. The improvement set forth in claim 8 in which said means securing the corredponding optical element in place within said longitudinal axial bore comprises an epoxy extending into the corresponding transverse bore and engaged with the corresponding optical element.

10. The improvement set forth in claim 1 in which said main body has a longitudinal axis and said one and said another body portions are circular cylindrical elements of the same outside diameter coaxial with said axis separably joined at respective confronting axial ends thereof, said two elements being separably joined by said press-fit connection comprising a circular cylindrical axial projection in one of said confronting axial ends press-fitted into a corresponding circular cylindrical axial receptacle in the other of said confronting axial ends, said confronting ends and press-fit connection being constructed and arranged such that there is a very slight separation between radially outer circumferentially extending marginal portions of said confronting axial ends when said projection is fully press-fitted within said receptacle, at least one of said fluid inlet and outlet ports being disposed in the circular cylindrical outside diameter of the corresponding body portion.

11. The improvement set forth in claim 10 in which said main body comprises a longitudinal axial bore open at opposite axial ends of said main body, said bore being coaxial with said axis, one portion of said longitudinal axial bore being in said another body portion, said optical entrance comprising an optical element disposed in said longitudinal axial bore at one axial end thereof and said optical exit comprising an optical element disposed in said longitudinal axial bore at the opposite axial end thereof whereby one optical element is disposed in said one body portion and the other optical element is disposed in said another body portion, said portion of said fluid passage being that portion of said longitudinal axial bore which lies axially between said two optical elements, said fluid passage also comprising radial sections each extending radially from said longitudinal axial bore respectively to a respective one of said fluid inlet and said fluid outlet ports, said fluid inlet and outlet ports both being disposed each in the circular cylindrical outside diameter of the corresponding body portion, said radial sections of said fluid passage intercepting said longitudinal axial bore at axially spaced apart locations lying between said optical elements, said optical elements comprising circular cylindrical rods disposed to fit closely within the longitudinal axial bore, and means for securing said optical elements in place within said longitudinal axial bore.

12. The improvement set forth in claim 11 in which each of said one and said another body portions is provided with indicia correlating said one and said another body portions for use with each other to establish a corresponding length of said optical path identified by said indicia.

13. The improvement set forth in claim 12 in which said main body comprises acrylic plastic, said radial sections of said fluid passage being constructed and arranged for reception of one end of a circular tubular metal element, and a circular tubular metal element disposed within each of said radial sections and projecting radially outwardly beyond the plastic main body to provide for connection to a corresponding external fluid conduit.

14. The improvement set forth in claim 1 further including a holder in combination with said flowcell, said flowcell main body having a circular cylindrical outside diameter, said inlet and outlet ports comprising fittings projecting radially outwardly beyond the outside diameter of said main body of said flowcell, said holder comprising a body provided with a bore corresponding to the outside diameter of the main body of the flowcell to circumferentially embrace same, said holder also including a throat extending radially outwardly from the outer perimeter of its bore to open to an outer surface of the receptacle, said throat being dimensioned to allow said fittings to pass axially therethrough as the main body of the flowcell is being moved axially through said holder bore when said fittings are circumferentially aligned with the throat of said holder.

15. The improvement set forth in claim 14 in which the holder is further provided with sockets adapted for reception of mating projections for mounting of the holder on a base whereby the holder will support the flowcell in space relation from the point of mounting of the holder on the base.

16. In combination, a flowcell having a main longitudinal axis and comprising a main body provided with a fluid inlet port, a fluid outlet port, and a fluid passage extending through said main body between said fluid inlet and fluid outlet ports, said main body having a circular cylindrical outside diameter and also being provided with a light entrance, a light exit, and an optical path extending through said main body between said light entrance and said light exit including a portion of said fluid passage, inlet and outlet fittings at the respective fluid inlet and fluid outlet ports which fittings at the respective fluid inlet and fluid outlet ports which fittings project radially outwardly of the main body of the flowcell and a holder for the flowcell comprising a holder body provided with a circular bore corresponding to the diameter of the main body of the flowcell so as to hold the flowcell by circumferentially embracing the main body of the flowcell, said holder including a throat extending from its bore and open to an outer surface of the holder, said holder being constructed such that its throat is dimensioned in relation to at least one of the inlet and outlet fittings to allow that at least one fitting to pass axially through the throat when it is circumferentially aligned with the throat as the flowcell body is axially moved through the holder bore.

17. In the combination of claim 16, said main body of the flowcell comprising separably joined body portions each containing a corresponding one of said inlet and outlet fittings, said body portions being joinable at any relative circumferential orientation over a full 360° about said axis.

* * * * *